(12) United States Patent
Fujisawa et al.

(10) Patent No.: US 8,080,622 B2
(45) Date of Patent: Dec. 20, 2011

(54) SOLUBLE SILICONE PREPOLYMERS

(75) Inventors: Kazuhiko Fujisawa, Otsu (JP); Mitsuru Yokota, Otsu (JP); Masataka Nakamura, Otsu (JP)

(73) Assignees: Johnson & Johnson Vision Care, Inc., Jacksonville, FL (US); Toray Industries Inc., Tokyo (JP)

( * ) Notice: Subject to any disclaimer, the term of this patent is extended or adjusted under 35 U.S.C. 154(b) by 0 days.

(21) Appl. No.: 11/771,999

(22) Filed: Jun. 29, 2007

(65) Prior Publication Data

US 2009/0005528 A1    Jan. 1, 2009

(51) Int. Cl.
*C07F 7/08* (2006.01)
*C07F 7/10* (2006.01)
*C08F 130/08* (2006.01)

(52) U.S. Cl. ......... 526/279; 556/400; 556/413; 556/419

(58) Field of Classification Search .......... 526/279
See application file for complete search history.

(56) References Cited

U.S. PATENT DOCUMENTS

| | | | |
|---|---|---|---|
| 2,793,223 A | 5/1957 | Merker | |
| 2,956,044 A | 10/1960 | Merker | |
| 3,057,902 A | 10/1962 | Pike | |
| 3,563,742 A | 2/1971 | Phlipot et al. | 96/28 |
| 3,756,820 A | 9/1973 | Hayakawa et al. | |
| 3,859,320 A | 1/1975 | Atherton | |
| 3,865,588 A | 2/1975 | Ohto et al. | |
| 3,959,358 A | 5/1976 | Jursich | |
| 4,117,001 A | 9/1978 | Fozzard | |
| 4,120,570 A | 10/1978 | Gaylord | |
| 4,139,692 A | 2/1979 | Tanaka et al. | 526/218 |
| 4,235,985 A | 11/1980 | Tanaka et al. | 526/279 |
| 4,259,467 A | 3/1981 | Keogh et al. | 526/279 |
| 4,260,725 A | 4/1981 | Keogh et al. | 526/279 |
| 4,395,496 A | 7/1983 | Wittmann et al. | |
| 4,402,887 A | 9/1983 | Kuriyama et al. | |
| 4,463,149 A | 7/1984 | Ellis | |
| 4,563,538 A | 1/1986 | Wakabayashi et al. | |
| 4,632,968 A | 12/1986 | Yokota et al. | 526/279 |
| 4,853,453 A | 8/1989 | Schafer et al. | 528/28 |
| 4,861,850 A | 8/1989 | Novicky | |

(Continued)

FOREIGN PATENT DOCUMENTS

CN    200780043363.1    9/2007

(Continued)

OTHER PUBLICATIONS

Adams, et al., "Metal Segregation in Bimetallic Clusters and Its Possible Role in Synergism and Bifunctional Catalysis," 2000, Journal of Organometallic Chemistry, vol. 600, p. 1-6.

(Continued)

*Primary Examiner* — Robert Loewe
(74) *Attorney, Agent, or Firm* — Ballard Spahr LLP (57) ABSTRACT

In one aspect, the invention relates to silicon-based prepolymers. The disclosed prepolymers exhibit satisfactory solubility in aqueous solutions or hydrophilic solutions and can overcome undesirable shrinkage, expansion, and related problems possessed by conventional silicone monomers and related conventional polymerization techniques by producing hydrogels from a crosslinkable prepolymer. Also disclosed are polymers and molded articles produced from the disclosed prepolymers, which attain a satisfactory oxygen permeability. Also disclosed are methods for producing the disclosed prepolymers. This abstract is intended as a scanning tool for purposes of searching in the particular art and is not intended to be limiting of the present invention.

16 Claims, 2 Drawing Sheets

U.S. PATENT DOCUMENTS

| | | | |
|---|---|---|---|
| 5,010,141 A | 4/1991 | Mueller | 525/276 |
| 5,045,233 A | 9/1991 | Kita et al. | |
| 5,045,621 A | 9/1991 | Suzuki et al. | 528/14 |
| 5,057,578 A | 10/1991 | Spinelli | 525/278 |
| 5,079,319 A | 1/1992 | Mueller | 526/238.23 |
| 5,128,484 A | 7/1992 | Kita et al. | |
| 5,219,965 A | 6/1993 | Valint, Jr. et al. | 526/245 |
| 5,314,960 A | 5/1994 | Spinelli et al. | 525/280 |
| 5,321,108 A | 6/1994 | Kunzler et al. | 526/242 |
| 5,329,034 A | 7/1994 | Nagase et al. | |
| 5,336,797 A | 8/1994 | McGee et al. | 556/419 |
| 5,371,147 A | 12/1994 | Spinelli et al. | 525/288 |
| 5,387,662 A | 2/1995 | Kunzler et al. | 526/245 |
| 5,387,663 A | 2/1995 | McGee et al. | 526/279 |
| 5,470,930 A | 11/1995 | Toba et al. | 526/204 |
| 5,481,015 A | 1/1996 | Nomura | |
| 5,493,039 A | 2/1996 | Okawa et al. | |
| 5,510,428 A | 4/1996 | Harano et al. | 525/438 |
| 5,539,016 A | 7/1996 | Kunzler et al. | 523/107 |
| 5,554,706 A | 9/1996 | Nagase et al. | |
| 5,563,184 A | 10/1996 | McGee et al. | 523/107 |
| 5,831,110 A | 11/1998 | Isoda et al. | |
| 5,888,356 A | 3/1999 | Keil et al. | |
| 5,891,977 A | 4/1999 | Dietz et al. | |
| 5,962,548 A * | 10/1999 | Vanderlaan et al. | 523/107 |
| 5,994,488 A * | 11/1999 | Yokota et al. | 526/279 |
| 6,031,059 A | 2/2000 | Vanderlaan et al. | |
| 6,177,585 B1 | 1/2001 | Chen et al. | 556/479 |
| 6,180,741 B1 | 1/2001 | Yamaguchi et al. | 526/301 |
| 6,218,503 B1 | 4/2001 | Lai et al. | 528/320 |
| 6,306,992 B1 | 10/2001 | Yoshitake et al. | 526/279 |
| 6,334,935 B1 | 1/2002 | Uehara et al. | 203/8 |
| 6,344,495 B1 * | 2/2002 | Ueda et al. | 522/96 |
| 6,350,816 B1 * | 2/2002 | Farronato et al. | 525/326.1 |
| 6,372,815 B1 | 4/2002 | Sule et al. | 523/106 |
| 6,617,373 B2 | 9/2003 | Sule et al. | 523/108 |
| 6,649,722 B2 * | 11/2003 | Rosenzweig et al. | 526/279 |
| 6,783,897 B2 | 8/2004 | Kang et al. | |
| 6,787,615 B2 | 9/2004 | Keller et al. | |
| 6,822,016 B2 * | 11/2004 | McCabe et al. | 523/107 |
| 6,846,892 B2 | 1/2005 | Kindt-Larsen et al. | 526/320 |
| 6,922,118 B2 | 7/2005 | Kubena et al. | 333/188 |
| 6,933,401 B2 | 8/2005 | Molock et al. | |
| RE39,635 E | 5/2007 | Vanderlaan et al. | |
| 7,317,117 B2 | 1/2008 | Nakamura et al. | |
| 7,368,589 B2 * | 5/2008 | Mahadevan et al. | 556/466 |
| 7,461,937 B2 * | 12/2008 | Steffen et al. | 351/160 H |
| 2002/0016383 A1 | 2/2002 | Iwata et al. | 523/106 |
| 2003/0109661 A1 | 6/2003 | Salamone et al. | 528/25 |
| 2003/0130465 A1 | 7/2003 | Lai et al. | 528/25 |
| 2004/0014921 A1 * | 1/2004 | Fujisawa et al. | 526/303.1 |
| 2004/0106694 A1 | 6/2004 | Fujisawa et al. | |
| 2004/0114101 A1 | 6/2004 | Thakrar | |
| 2004/0198916 A1 | 10/2004 | Nakamura et al. | |
| 2004/0198938 A1 | 10/2004 | Nakamura et al. | |
| 2004/0201820 A1 * | 10/2004 | Nakamura et al. | 351/159 |
| 2004/0249180 A1 | 12/2004 | Nakamura et al. | |
| 2005/0165246 A1 | 7/2005 | Lai et al. | 556/413 |
| 2005/0237483 A1 * | 10/2005 | Phelan | 351/162 |
| 2006/0007391 A1 | 1/2006 | McCabe et al. | |
| 2006/0047134 A1 | 3/2006 | Molock et al. | |
| 2006/0223964 A1 | 10/2006 | Lai et al. | 528/32 |
| 2006/0229423 A1 | 10/2006 | Parakka et al. | |
| 2007/0203275 A1 | 8/2007 | Kikuchi et al. | |
| 2008/0004383 A1 | 1/2008 | Nakamura et al. | |
| 2008/0004401 A1 * | 1/2008 | Nakamura et al. | 525/223 |
| 2008/0081850 A1 * | 4/2008 | Fujisawa et al. | 523/106 |
| 2008/0081894 A1 * | 4/2008 | Fujisawa et al. | 528/33 |
| 2008/0119627 A1 * | 5/2008 | Nakamura et al. | 528/31 |
| 2008/0143003 A1 * | 6/2008 | Phelan | 264/1.36 |

FOREIGN PATENT DOCUMENTS

| | | |
|---|---|---|
| CN | 200780044049.5 | 9/2007 |
| EP | 0 733 637 | 9/1996 |
| EP | 0 753 521 | 1/1997 |
| EP | 0 965 593 | 12/1999 |
| EP | 1 123 915 | 8/2001 |
| EP | 1 386 924 | 2/2004 |
| EP | 1 403 396 | 3/2004 |
| EP | 1 426 809 A1 | 6/2004 |
| EP | 1 719 776 | 11/2006 |
| EP | 1 749 812 | 2/2007 |
| EP | 07 874 059.4 | 6/2007 |
| EP | 07 838 814.7 | 9/2007 |
| EP | 07838800.6 | 9/2007 |
| GB | 1 364 360 | 8/1974 |
| JP | 50-014786 | 2/1975 |
| JP | 52-168545 | 12/1977 |
| JP | 55-015110 | 2/1980 |
| JP | 56-022325 | 3/1981 |
| JP | 63-301919 | 8/1988 |
| JP | 63216044 | 9/1988 |
| JP | 04-077489 | 3/1992 |
| JP | 06-032791 | 2/1994 |
| JP | 08-283342 | 10/1996 |
| JP | 2000191667 | 7/2000 |
| JP | 2000191730 | 7/2000 |
| JP | 2001048939 | 2/2001 |
| WO | WO/96/31792 | 10/1996 |
| WO | WO/01/71392 | 9/2001 |
| WO | WO/02/081532 | 10/2002 |
| WO | WO 03/014130 | 2/2003 |
| WO | WO 03/021336 | 3/2003 |
| WO | WO/03/022322 | 3/2003 |
| WO | WO 03/027123 | 4/2003 |
| WO | WO/03/040193 | 5/2003 |
| WO | WO/03/043668 | 5/2003 |
| WO | WO/03/066688 | 8/2003 |
| WO | WO/03/077792 | 9/2003 |
| WO | WO/2005/115958 | 5/2004 |
| WO | WO 2005/005368 | 1/2005 |
| WO | WO 2005/005445 | 1/2005 |
| WO | WO 2005/044829 | 5/2005 |
| WO | WO/2005/090364 | 9/2005 |
| WO | WO 2008/005398 | 1/2008 |

OTHER PUBLICATIONS

International Search Report for International Application No. PCT/US2007/015264 (mailed May 12, 2007).

International Search Report for International Application No. PCT/US2007/020683 (mailed Jan. 25, 2008).

International Search Report for International Application No. PCT/US2007/020668 (mailed Jan. 25, 2008).

International Search Report for International Application No. PCT/US2007/024325 (mailed Apr. 24, 2008).

Hirabayashi et al., "A facile preparation and cyclopropanation of 1-alkenylsilanols," Bulletin of the Chemical Society of Japan, 71(10):2409-2417 (1998).

HQMME Product Literature, Eastman Chemicals website (2008).

Kawakami et al., "Synthesis and characterization of liquid crystalline polystyrenes with disiloxane linkage in the spacer," *Polymer Bulletin (Berlin)*, 36(6):653-658 (1996).

Künzler, "Silicone Hydrogels for Contact Lens Application," *Trends in Polymer Science*, 4(2):52-59 (1996).

Lai, "Role of Bulky Polysiloxanylalkyl Methacrylates in Oxygen-Permeable Hydrogel Materials," *Journal of Applied Polymer Science*, 56(3):317-324 (1995).

Plueddemann et al., "Epoxyorganosilozanes," *J. Am. Chem Soc.*, 81:2632-2635 (1959).

Volkova et al., "Reaction of dimethylsiloxacyclohexane with methacrylic acid and triethylsilanol: Synthesis of [(mehtacryloyloxy)butyl]dimethyl(triethylsiloxy)silane," *Zhurnal Obshchei Khimii*, 58(9):2145-2148 (1988).

Fortuniak, "Controlled Synthesis of Siloxan Polymers and Siloxan-Siloxane Block Copolymers with 3-Chloropropyl Groups Pendat to the Siloxane Chain," Macromol. Chem. Phys. 2001, 202, 2306-2313.

Gaylord, "Composition for Manufacturing Contact Lenses," Accession No. 1976:578430, based on Brazilian Patent No. 7403534.

Material Safety Data Sheet of 2-Ethylhexyl acrylate, Japan Petrochemical Industry Association, May 25, 1986 (revised in Aug. 2001), p. 4-5, Item 10, 11.1-10, available at http://www.jpca.or.jp/61msds/j7cb32.htm (accessed Jul. 17, 2008).

U.S. Appl. No. 11/609,677, filed Dec. 12, 2006, Nakamura, Response to the Rejection mailed by the PTO on May 11, 2009, Nov. 11, 2009.
U.S. Appl. No. 11/609,724, filed Dec. 12, 2006, Nakamura, Final Rejection mailed by the PTO on Nov. 9, 2009.
U.S. Appl. No. 11/561,456, filed Nov. 20, 2006, Fujisawa, Non-Final Rejection mailed by the PTO on Oct. 27, 2009.
U.S. Appl. No. 11/681,406, filed Mar. 2, 2007, Nakamura, Response to the Final Rejection mailed by the PTO on Jul. 6, 2009, Jan. 6, 2010.
U.S. Appl. No. 11/609,724, filed Dec. 12, 2006, Nakamura, Amendment Received in the PTO on Aug. 18, 2009.
U.S. Appl. No. 11/561,456, filed Nov. 20, 2006, Fujisawa, Response to the Requirement for Restriction/Election received in the PTO on Aug. 11, 2009.
U.S. Appl. No. 11/561,525, filed Nov. 20, 2006, Fujisawa, Examiner Interview Summary, Jul. 31, 2009.
U.S. Appl. No. 11/561,525, filed Nov. 20, 2006, Fujisawa, Non-Final Rejection mailed by the PTO on Sep. 14, 2009.
U.S. Appl. No. 11/681,406, filed Mar. 2, 2007, Nakamura, Final Rejection mailed by the PTO on Jul. 6, 2009.
PCT/US2008/088287, filed Dec. 24, 2008, Fujisawa, Written Opinion, Apr. 28, 2009.
PCT/US2008/088287, filed Dec. 24, 2008, Fujisawa, International Search Report, Apr. 28, 2009.
U.S. Appl. No. 11/609,724, filed Dec. 12, 2006, Nakamura, Amendment received in the PTO on Apr. 15, 2010.
U.S. Appl. No. 12/060,536, filed Apr. 1, 2008, Fujisawa, Non-Final Rejection mailed by the PTO on Mar. 18, 2010.
EP 08772142.9, filed Jun. 27, 2008, Fujisawa, Preliminary Amendment, Mar. 19, 2010.
U.S. Appl. No. 11/609,677, filed Dec. 12, 2006, Nakamura, Amendment received in the PTO on Aug. 16, 2010.
U.S. Appl. No. 11/561,456, filed Nov. 20, 2006, Fujisawa, Final Rejection mailed by the PTO on May 26, 2010.
U.S. Appl. No. 11/561,456, filed Nov. 20, 2006, Fujisawa, Amendment received in the PTO on Jun. 28, 2010.
U.S. Appl. No. 11/561,456, filed Nov. 20, 2006, Fujisawa, Notice of Allowance Issued, Jul. 8, 2010.
U.S. Appl. No. 11/561,525, filed Nov. 20, 2006, Fujisawa, Final Rejection mailed by the PTO on May 24, 2010.
U.S. Appl. No. 11/561,525, filed Nov. 20, 2006, Fujisawa, Office Action mailed Jan. 4, 2011.
U.S. Appl. No. 11/609,677, filed Dec. 12, 2006, Nakamura, Office Action mailed Nov. 9, 2010.
U.S. Appl. No. 11/609,724, filed Dec. 12, 2006, Nakamura, Office Action mailed Sep. 2, 2010.
U.S. Appl. No. 11/561,525, filed Nov. 20, 2006, Fujisawa, Response to final Office Action mailed May 24, 2010, Nov. 24, 2010.
U.S. Appl. No. 12/060,536, filed Apr. 1, 2008, Fujisawa, Response to Office Action mailed Mar. 18, 2010, Sep. 20, 2010.
U.S. Appl. No. 12/060,536, filed Apr. 1, 2008, Fujisawa, Notice of Allowance mailed Oct. 19, 2010.
U.S. Appl. No. 11/609,677, filed Dec. 12, 2006, Nakamura, Response to Office Action mailed Nov. 9, 2010, May 3, 2011.
U.S. Appl. No. 11/609,724, filed Dec. 12, 2006, Nakamura, Final Rejection mailed Mar. 29, 2011.
U.S. Appl. No. 12/901,191, filed Oct. 8, 2010, Fujisawa, Office Action mailed Apr. 27, 2011.
U.S. Appl. No. 11/609,724, filed Dec. 12, 2006, Nakamura, Response to Office Action mailed Sep. 2, 2010, Mar. 2, 2011.
U.S. Appl. No. 11/609,677, filed Dec. 12, 2006, Nakamura, Notice of Allowance mailed.
U.S. Appl. No. 11/561,525, filed Nov. 20, 2006, Fujisawa, Response to Office Action mailed Jan. 4, 2011.

* cited by examiner

SOLUBLE SILICONE PREPOLYMERS

BACKGROUND

Contact lenses have been used commercially to improve vision since the 1950s. Many current contact lenses are made of hydrogels formed by polymerizing hydrophilic monomers such as hydroxyethylmethacrylate (HEMA) and vinylpyrrolidone in the presence of a minor amount of a crosslinking agent.

Conventional silicone monomers are typically hydrophobic, making dissolution in aqueous solutions or hydrophilic solutions, such as e.g. poly(ethylene glycol)/poly(vinyl pyrrolidone) (PEG/PVP), difficult. That is, conventional silicone prepolymers prepared from conventional silicone monomers lack satisfactory solubility. For example, silicone prepolymers lacking polar silicone monomer residues (see, e.g., comparative example 3, infra), silicone prepolymers having too few polar silicone units (see, e.g., comparative example 1, infra), and silicone prepolymers having too many polar silicone units (see, e.g., comparative example 2, infra) are typically insoluble in PVP/PEG solution. Further, conventional silicone monomers having very low silicon monomer residue contents (see, e.g., comparative example 4, infra), while at least partially soluble in PVP/PEG because the total amount of silicone monomer is relatively small, can suffer from unsatisfactory oxygen permeability. Moreover, the polymerization of conventional monomers when forming molded articles (e.g., contact lenses) typically results in shrinkage, which may be as much as 20% by volume.

Therefore, there remains a need for methods and compositions that overcome these deficiencies and that effectively provide soluble materials that exhibit minimal shrinkage when forming molded articles and that also provide molded articles exhibiting satisfactory oxygen permeability.

SUMMARY

As embodied and broadly described herein, the invention, in one aspect, relates to silicon-based prepolymers.

In one aspect, the invention relates to prepolymers that can overcome undesirable shrinkage, expansion, and related problems possessed by conventional silicone monomers and related conventional polymerization techniques by producing hydrogels from a crosslinkable prepolymer.

In a further aspect, the invention relates to prepolymers further comprising at least one polar moiety, thereby achieving satisfactory solubility in aqueous solutions or hydrophilic solutions.

In a further aspect, the invention relates to prepolymers that have a silicon content of from about 10% to about 30% by weight, of the prepolymer and a polar silicone-containing residue content of from about 30% to about 90% by weight of the prepolymer, thereby attaining a satisfactory oxygen permeability.

In a further aspect, the invention relates to polymers and molded articles produced from the disclosed prepolymers.

In a further aspect, the invention relates to methods for producing the disclosed prepolymers.

In a further aspect, the invention relates to products of the disclosed methods.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments and together with the description illustrate the disclosed compositions and methods.

DETAILED DESCRIPTION

The present invention can be understood more readily by reference to the following detailed description of the invention and the Examples included therein.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein may be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a component," "a polymer," or "a residue" includes mixtures of two or more such components, polymers, or residues, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

It is also understood that each unit between two particular units are also disclosed. For example, if 10 and 15 are disclosed, then 11, 12, 13, and 14 are also disclosed.

As used herein, the term "residue" of a chemical species refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "prepolymer" refers to a polymer of relatively low molecular weight, usually intermediate between that of the monomer and the final polymer or resin, which may be mixed with compounding additives, and which is capable of being hardened by further polymerization during or after a forming process.

As used herein, the term "hydrophilic group" refers to a moiety having an affinity for water or a hydrophilic solvent. Suitable examples include a residue of a hydrophilic monomer (e.g., 2-hydroxyethyl(meth)acrylate) and residues of residues of N,N-dimethylacrylamide, 2-hydroxyethyl methacrylate, N-vinylpyrrolidone, N-vinylformamide, N-vinylacetamide, (meth)acrylic acid, N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, or N-vinylimidazole As used herein, the term "polymerizable residue" refers to a chemical functionality capable of undergoing a polymerization reaction or cross-linking reaction to form a higher molecular weight compound and/or a more highly cross-linked structure. Suitable examples include methacryloyloxy groups, acryloyloxy groups, methacryl amide groups, acryl amide groups, styryl groups, vinyl groups, vinyl carbonate groups, vinyl carbamate groups, allyl carbonate groups, or allyl carbamate groups.

As used herein, the term "siloxanyl" refers to a structure having at least one Si—O—Si bond. Thus, for example, siloxanyl group means a group having at least one Si—O—Si group, and siloxanyl compound means a compound having at least one Si—O—Si group.

As used herein, the term "siloxanyl monomer" refers to a siloxanyl compound having at least one polymerizable carbon-carbon unsaturated bond. In one aspect, the polymerizable carbon-carbon unsaturated bond can be part of an alkylacryloyl moiety (e.g., acryloyl or a methacryloyl moiety).

As used herein, the term "alkylacrylic acid" refers to acrylic acid, alkyl-substituted acrylic acids, salts thereof, and derivatives thereof. In one aspect, an alkylacrylic acid can be further substituted. In a further aspect, an alkylacrylic acid is methacrylic acid.

As used herein, the term "reduced pressure distillation" refers to the act of purifying liquids through evaporating or boiling at a pressure lower than about atmospheric pressure (i.e., about 1000 mbar or about 760 Torr), so that the gaseous vapors condense to a pure liquid. Pollutants and contaminants typically remain in a concentrated residue. The pressure can be, for example, less than about 100 mbar, less than about 10 mbar, less than about 1 mbar, less than about 0.1 mbar, less than about 0.05 mbar, or less than about 0.02 mbar. An apparatus for distilling typically includes a distilling vessel (which holds the pre-distillation material during heating), a condenser (which cools the evaporated material), and a receiving vessel (which collects the distillate). In one aspect, distillation does not include chemical vapor deposition.

As used herein, the term "thin film distillation" refers to short path distillation wherein a substantial decrease of boiling temperature is obtained by reducing the operating pressure. This can allow thermal separation of products that would be destroyed by conventional vacuum distillation (pot still or distillation column) because of the necessary high temperatures and long residence time. In one aspect, this term refers to a distillation operation in which a thin layer of liquid is subjected to distillation. Therefore, the operations generally called thin film distillation, molecular distillation, short path distillation, thin film evaporation, short path evaporation, and the like, are within the scope of "thin film distillation."

As used herein, the term "polymerization inhibitor," sometimes also referred to as a "radical inhibitor" or a "radical scavenger," refers to a substance that impedes or retards the process of polymerization. Typically, such an inhibitor slows or prevents the formation of radicals, which can initiate polymerization. Alternatively, such an inhibitor can react with any formed radicals at a rate greater than the polymerization initiation and/or propagation steps. Examples of suitable polymerization inhibitors include alkylhydroquinones and hydroxynaphthalenes.

In one aspect, a polymerization inhibitor can be present during the distillation of the disclosed materials. In a further aspect, a polymerization inhibitor can be present in the distilling vessel of the distillation. In a yet further aspect, a polymerization inhibitor can be selected so as to undergo volatization during the distillation process. In an even further aspect, a polymerization inhibitor can be selected so as to not volatize during the distillation process. In a still further aspect, a polymerization inhibitor can be present in the receiving vessel of the distillation.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. Unless explicitly disclosed, this disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example 1 to 12 carbon atoms or 1 to 6 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol $C=C$. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., $C=C$. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an interger from 1 to 500. "Polyester" is the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halide" and "halo" as used herein refer to the halogens fluorine, chlorine, bromine, and iodine.

The terms "hydroxy" and "hydroxyl" as used herein is represented by the formula —OH.

The term "ketone" and "keto" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The terms "nitrile" and "cyano" as used herein are represented by the formula —CN.

The term "silyl" as used herein is represented by the formula —Si$A^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to one or more silicone prepolymers. More specifically, compounds are disclosed wherein undesirable shrinkage, expansion, and related problems possessed by conventional silicone monomers and related conventional polymerization techniques can be overcome by producing hydrogels from a crosslinkable prepolymer having a relatively low molecular weight and low polydispersity. Moreover, the disclosed prepolymers are prepared having structures that provide satisfactory solubilities in aqueous solutions or hydrophilic solutions, such as PEG/PVP, as well as satisfactory oxygen permeabilities.

1. Structure

In one aspect, a prepolymer can be a compound or collection of compounds comprising at least one silicone-containing residue having a structure represented by the formula:

wherein $R^a$ represents hydrogen or methyl, and wherein A represents a siloxanyl group; and at least one polymerizable residue having a structure represented by the formula:

wherein $R^p$ represents hydrogen or methyl, and wherein P represents an organic group comprising at least one polymerizable moiety; wherein the prepolymer has a silicon content of from about 10% to about 30% by weight, of the prepolymer; wherein at least one of the at least one silicone-containing residue is a polar silicone-containing residue further comprising at least one polar moiety; and wherein the prepolymer has a polar silicone-containing residue content of from about 30% to about 90% by weight of the prepolymer.

a. Siloxanyl Groups

In one aspect, the disclosed prepolymers comprise one or more siloxanyl groups. Unless otherwise specifically described, a siloxanyl group can be any siloxanyl group known to those of skill in the art.

In a further aspect, at least one A has a structure represented by the formula:

wherein L represents a $C_1$-$C_{20}$ alkyl residue or a $C_1$-$C_{20}$ aryl residue; and wherein D represents a siloxanyl group. In a still further aspect, at least one A has a structure represented by the formula:

wherein G represents a $C_1$-$C_{20}$ alkyl residue or a $C_1$-$C_{20}$ aryl residue, which alkyl residue or aryl residue further comprises at least one hydroxyl group; wherein L represents a $C_1$-$C_{20}$ alkyl residue or a $C_1$-$C_{20}$ aryl residue; and wherein D represents a siloxanyl group.

In a further aspect, D has a structure represented by the formula:

wherein $E^1$ to $E^{11}$ independently represent hydrogen, an optionally substituted $C_1$-$C_{20}$ alkyl residue, or an optionally substituted $C_6$-$C_{20}$ aryl residue; wherein h represents an integer of from 0 to 200; and wherein i, j, and k independently represent integers of from 0 to 20, with the proviso that h, i, j and k are not simultaneously zero.

In a further aspect, at least one A has a structure represented by the formula:

wherein n represents an integer of from 3 to 10; and wherein $R_s$ represents a $C_1$-$C_{20}$ alkyl residue or a $C_1$-$C_{20}$ aryl residue.

b. Hydrophilic Residues

In one aspect, the disclosed prepolymers comprise one or more hydrophilic residues. Unless otherwise specifically described, a hydrophilic residue can be any hydrophilic residue known to those of skill in the art. In certain aspects, hydrophilic residues can be absent from the disclosed prepolymers.

In a further aspect, a prepolymer can further comprise at least one at least one hydrophilic residue having a structure represented by the formula:

wherein $R^b$ represents hydrogen or methyl; and wherein B represents a hydrophilic group.

In a further aspect, a hydrophilic residue comprises one or more residues of N,N-dimethylacrylamide, 2-hydroxyethyl methacrylate, N-vinylpyrrolidone, N-vinylformamide, N-vinylacetamide, (meth)acrylic acid, N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, or N-vinylimidazole.

c. Polar Moieties

In one aspect, the disclosed prepolymers comprise one or more polar moieties. Unless otherwise specifically described, a polar moiety can be any polar moiety known to those of skill in the art. In a further aspect, a polar moiety can be hydroxyl, amide, carboxyl, amino, carbonate, carbamate, sulfonamide, sulfonic, phosphonic, methoxyethyl, methoxyethoxyethyl, hydroxyethyl, or hydroxyethoxyethyl.

d. Polymerizable Residues

In one aspect, the disclosed prepolymers comprise one or more polymerizable residues or groups. Unless otherwise specifically described, a polymerizable residue can be any polymerizable residue known to those of skill in the art. In a further aspect, a polymerizable residue comprises one or more ethylenically unsaturated moieties, for example, a methacryloyloxy group, an acryloyloxy group, a methacryl amide group, an acryl amide group, a styryl group, a vinyl group, a vinyl carbonate group, a vinyl carbamate group, an allyl carbonate group, or an allyl carbamate group.

In a further aspect, a polymerizable residue is obtained by reacting a unit having a structure represented by the formula:

wherein $R^z$ represents hydrogen or methyl; wherein Z represents an optionally substituted $C_1$-$C_{20}$ alkyl residue or an optionally substituted $C_6$-$C_{20}$ aryl residue, which alkyl or aryl further comprises at least one of an hydroxyl group, a carboxyl group, an ester group, or a carboxylic anhydride group; with at least one compound having at least one polymerizable residue.

In a further aspect, Z comprises one or more of:

a halogenocarbonyl group, a (meth)acryloyloxycarbonyl group, a carboxyl group, a $C_1$-$C_{20}$ alkyloxycarbonyl group, a 2-aminoethoxycarbonyl group, a 4-halogenocarbophenyl group, a 4-carboxyphenyl group, or a 4-($C_1$-$C_{20}$ alkyloxycarbonyl)phenyl group.

In one aspect, the compound having at least one polymerizable group is 2-isocyanatoethyl(meth)acrylate, (meth)acryloyl isocyanate, (meth)acrylic acid halide, (meth)acrylic anhydride, (meth)acrylic acid, methyl(meth)acrylate, ethyl(meth)acrylate, 2-hydroxyethyl(meth)acrylate, 2-aminoethyl(meth)acrylate, 4-vinylbenzoic acid halide, 4-vinylbenzoic anhydride, or 4-vinylbenzoic acid ester.

In a further aspect, at least one polymerizable moiety has a structure represented by the formula:

wherein R represents hydrogen or methyl.

e. Terminal Groups

It is understood that the disclosed prepolymers can have terminal groups resulting from the initiation and termination of the polymerization reaction used to prepare the prepolymer. For example, a prepolymer can have a terminal group resulting from the initiation reaction and having a structure represented by a formula:

wherein A, B, and P represent a siloxanyl group, a hydrophilic group, and a polymerizable group, as described herein. In the above structures, the symbol IN represents a residue of an initiator, for example, an azo initiator or a peroxide initiator.

A prepolymer can also have a terminal group resulting from the termination reaction and having a structure represented by a formula:

wherein A, B, and P represent a siloxanyl group, a hydrophilic group, and a polymerizable group, as described herein. In the above structures, the symbol T represents a residue of a terminator, for example, a hydrogen atom extracted from water or other protic solvent.

It is also understood that the disclosed prepolymers can have analogous terminal groups resulting from analogous initiation and termination reactions with comonomers.

2. Silicon Content

In one aspect, a disclosed prepolymer can have a silicon content of from about 10% to about 30% by weight. In a further aspect, a disclosed prepolymer can have a silicon content of from about 13% to about 20% by weight. For example, the silicon content can be from about 15% to about 20%, from about 13% to about 18%, from about 15% to about 18%, about 13%, about 15%, about 18%, or about 20%. It is also understood that a disclosed silicon content can represent the average silicon content for a collection of silicone prepolymers.

In a further aspect, the total of the polar silicone units can be from about 50% to about 80% by weight, based on solid content of the prepolymer. For example, the total of the polar silicone units can be from about 55% to about 80%, from about 60% to about 80%, from about 50% to about 75%, from about 50% to about 70%, from about 60% to about 70%, or from about 55% to about 75%. It is also understood that a disclosed total of the polar silicone units can represent the average total for a collection of silicone prepolymers.

In a further aspect, the content of the polymerizable unit can be from about 0.1 to about 15 mol %, based on the prepolymer. For example, the content of the polymerizable unit can be from about 0.25 mol % to about 15 mol %, from about 0.5 mol % to about 15 mol %, from about 1 mol % to about 15 mol %, from about 0.1 mol % to about 12 mol %, from about 0.1 mol % to about 10 mol %, from about 0.1 mol % to about 5 mol %, or from about 0.1 mol % to about 10 mol %. It is also understood that a disclosed content of the polymerizable unit can represent the average content of the polymerizable unit for a collection of silicone prepolymers.

3. Solubility

In one aspect, the disclosed prepolymers exhibit superior solubility in aqueous solutions or hydrophilic solutions, such as e.g. PEG/PVP. Solubility can be determined by solubility tests in which a sample of the prepolymer is stored in a number of different solvents. By observing whether the polymer is dissolved, swelled, or unchanged, it is possible to ascertain whether and to what extent a prepolymer is soluble in a given solvent system. See Hansen Solubility Parameters; A User's Handbook, Charles M. Hansen, pp. 43-53, CRC Press 2000. For example, a known mass of prepolymer can be exposed to an excess amount of a given solvent system for a period of time (e.g., 10 minutes). The mixture can be optionally sonicated and/or exposed to elevated temperature. Afterwards, any undissolved prepolymer can be removed by decantation or by filtration, and the proportion dissolved within the solvent system can be calculated.

Solubility can be determined by using a protocol of the following example (note that wt % is an example for 60 wt % solid solution): (1) Irgacure 819 (a photo-initiator, 0.42 wt %) and a prepolymer (55.38 wt %) are added into PEG (40 wt %)/PVP (4.2 wt %) solution. (2) The mixture is mixed well with a touch mixer and by sonication. (3) The mixture is put in an oven at 70° C. for about one hour. (4) The mixture removed from the oven and mixed with a spatula. (5) The mixture is put in the oven again for another 40 minutes. (6) Repeat steps 4 and 5. (7) If the mixture is clear and phase separation is not observed when the mixture is taken out from the oven, it is considered "soluble." If the mixture is hazy or phase separation is observed, it is considered "insoluble."

In one aspect, a prepolymer can have a solubility of not less than about 50% by weight, based on solid content of the prepolymer, in a water-soluble solvent. For example, the solubility can be at least about 55%, at least about 60%, at least about 65%, at least about 70%, at least about 75%, at least about 80%, at least about 85%, or at least about 90%. It is understood that, in one aspect, the solubility can be affected by the average molecular weight of the prepolymer composition. That is, prepolymer having a certain molecular weight or less can be soluble, while prepolymer having a certain molecular weight or more can be less soluble.

In one aspect, prepolymer can have a solubility of not less than about 50% by weight (e.g., at least about 55%, at least about 60%, at least about 65%, at least about 70%, at least about 75%, at least about 80%, at least about 85%, or at least about 90%), based on solid content of the prepolymer, in a water-soluble solvent comprising from about 1% to about 10% (e.g., from about 1% to about 5%, from about 5% to about 10%, from about 2% to about 8%, about 2%, about 3%, about 4%, about 5%, about 6%, about 7%, about 8%, or about 9%) by weight of polyvinylpyrrolidone.

Solvent systems suitable for use with the disclosed prepolymers are typically water-soluble solvents and include ethylene glycol, propylene glycol, polyethylene glycol, polypropylene glycol, ethylene glycol-propylene glycol copolymer, and a mixture thereof.

4. Molecular Weight

In one aspect, the disclosed prepolymers can have an average molecular weight of from about 10 kD to about 1000 kD, for example from about 10 kD to about 500 kD, from about 10 kD to about 300 kD, or from about 10 kD to about 200 kD. In one aspect, the polydispersity ($M_w/M_n$) of the disclosed prepolymers can be from about 1.00 to about 10.00. For example, the polydispersity can be from about 1.00 to about 9.00, from about 1.00 to about 8.00, from about 1.00 to about 7.00, from about 1.00 to about 6.00, or from about 1.00 to about 5.00. In a further aspect, the polydispersity can be less than about 8, for example, less than about 7.5, less than about 7, less than about 6.5, less than about 6, less than about 5.5, less than about 5, less than about 4.5, or less than about 4.

5. Comonomers

It is also contemplated that the disclosed prepolymers can further comprise residues from further comonomers, so long as the prepolymer retains a silicon content of from about 10% to about 30% by weight, of the prepolymer and a polar silicone-containing residue content of from about 30% to about 90% by weight of the prepolymer. Preferred examples of such comonomers include alkyl (meth)acrylates such as (meth)acrylic acid, itaconic acid, crotonic acid, cinnamic acid, vinylbenzoic acid, methyl (meth)acrylate and ethyl (meth)acrylate; polyfunctional (meth)acrylates such as polyalkylene glycol mono(meth)acrylate, polyalkylene glycol monoalkyl ether (meth)acrylate, polyalkylene glycol bis(meth)acrylate, trimethylolpropane tris(meth)acrylate, pentaerythritol tetrakis(meth)acrylate, polydimethyl siloxane having (meth)acryloxypropyl group at both ends, polydimethyl siloxane having (meth)acryloxypropyl group at one end and polydimethyl siloxane having a plurality of (meth)acryloyl groups in side chains; halogenated alkyl (meth)acrylates such as trifluoroethyl(meth)acrylate and hexafluoroisopropyl (meth)acrylate; hydroxyalkyl(meth)acrylates having hydroxyl group such as 2-hydroxyethyl(meth)acrylate, 2-hydroxypropyl(meth)acrylate and 2,3-dihydroxypropyl(meth)acrylate; (meth)acrylamides such as N,N-dimethylacrylamide, N,N-diethylacrylamide, N,N-di-n-propylacrylamide, N,N-diisopropylacrylamide, N,N-di-n-butylacrylamide, N-acryloylmorpholine, N-acryloylpiperidine, N-acryloylpyrrolidine and N-methyl(meth)acrylamide; N-vinyl-N-methyl acetamide, N-vinyl-N-ethyl acetamide, N-vinyl-N-ethyl formamide, N-vinyl formamide, aromatic vinyl monomers such as styrene, α-methylstyrene and vinylpyridine; maleimides; heterocyclic vinyl monomers such as N-vinylpyrrolidone; 3-[tris(trimethylsiloxy)silyl]propyl(meth)acrylate, 3-[bis(trimethylsiloxy)methylsilyl]propyl(meth)acrylate, 3-[(trimethylsiloxy)dimethylsilyl]propyl(meth)acrylate, 3-[tris(trimethylsiloxy)silyl]propyl (meth)acrylamide, 3-[bis(trimethylsiloxy)methylsilyl]propyl (meth)acrylamide, 3-[(trimethylsiloxy)dimethylsilyl]propyl (meth)acrylamide, [tris(trimethylsiloxy)silyl]methyl(meth)acrylate, [bis(trimethylsiloxy)methylsilyl]methyl(meth)acrylate, [(trimethylsiloxy)dimethylsilyl]methyl(meth)acrylate, [tris(trimethylsiloxy)silyl]methyl(meth)acrylamide, [bis(trimethylsiloxy)methylsilyl]methyl(meth)acrylamide, [(trimethylsiloxy)dimethylsilyl]methyl(meth)acrylamide, [tris(trimethylsiloxy)silyl]styrene, [bis(trimethylsiloxy)methylsilyl]styrene, [(trimethylsiloxy)dimethylsilyl]styrene, polydimethyl siloxane having (meth)acryloxypropyl group at one end, and compounds represented by Formula (C1-1) to (C6-1) and (C1-2) to (C6-2) below.

(C1-1)

(C2-1)

(C3-1)

(C4-1)

(C5-1)

(C6-1)

(C1-2)

(C2-2)

(C3-2)

(C4-2)

(C5-2)

(C6-2)

Other silicone containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662; and 5,539,016 describe polysiloxanes with a polar fluorinated graft or side group having a hydrogen atom attached to a terminal difluoro-substituted carbon atom. US 2002/0016383 describe hydrophilic siloxanyl methacrylates containing ether and siloxanyl linkages and crosslinkable monomers containing polyether and polysiloxanyl groups.

In one embodiment comonomers include (meth)acrylic acid, 2-hydroxyethyl(meth)acrylate, 2-hydroxypropyl(meth)acrylate, N,N-dimethylacrylamide, N-vinyl pyrrolidone, N-vinyl-N-methyl acetamide, N-vinyl-N-ethyl acetamide, 3-[tris(trimethylsiloxy)silyl]propyl(meth)acrylate, 3-[bis(trimethylsiloxy)methylsilyl]propyl(meth)acrylate, the compounds C1-1, C2-1, C3-1, C4-1, C5-1, C6-1, C1-2, C2-2, C3-2, C4-2, C5-2, C6-2, polysiloxane macromers, hydrophilic siloxyanly methacrlyates containing ether and siloxanyl linkages and combinations thereof and the like.

Further preferred examples of such monomers include 2-propenoic acid, 2-methyl-2-hydroxy-3-[3-[1,3,3,3-tetramethyl-1-[(trimethylsilyl)oxy]disiloxanyl]propoxy]propyl ester (SiGMA); monomethacryloxypropyl-terminated mono-n-butyl terminated polydimethylsiloxane (mPDMS; MW 800-1000 ($M_n$)); bis-3-acryloxy-2-hydroxypropyloxypropyl polydimethylsiloxane (acPDMS) (MW 1000 and 2000, acrylated polydimethylsiloxane from Gelest and Degussa, respectively); methacryloxypropyl-terminated polydimethylsiloxane (MW 550-700) from Gelest (maP-DMS); and mono-(3-methacryloxy-2-hydroxypropyloxy)propyl terminated, mono-butyl terminated polydimethylsiloxane (mPDMS-OH).

C. Methods of Making the Compounds

In one aspect, the invention relates to a method of preparing a prepolymer. It is understood that the compounds, structures, and moieties disclosed in connection with the prepolymers can also be used in connection with the disclosed methods.

In one aspect, the disclosed prepolymers can be prepared by a method comprising the steps of providing a mixture comprising at least one monomer having a siloxanyl group, wherein at least one of the at least one monomer having a siloxanyl group is a polar silicone-containing monomer further comprising at least one polar moiety; at least one monomer having a polymerizable group; optionally, at least one comonomer (e.g., HEMA); and, optionally, at least one monomer having a hydrophilic group; reacting the monomers by heating the mixture at a reaction temperature (e.g., from about 50° C. to about 60° C.) for a reaction time (e.g., from about 2 hours to about 6 hours), and/or exposing the mixture to a radical initiator (e.g., 2,2'-azobis(2,4-dimethylvaleronitrile)), thereby polymerizing the monomers to provide an unfunctionalized intermediate polymer; combining the unfunctionalized intermediate polymer with a reactive compound (e.g., 2-isocyanate ethyl methacrylate) bearing an ethylenically unsaturated moiety (e.g., an acryloyl moiety); optionally, a polymerization inhibitor (e.g., 2,6-di-t-butyl-4-methylphenol); and, optionally, a catalyst (e.g., dibutyltindilauric acid); allowing the reactive compound to functionalize the unfunctionalized intermediate polymer, thereby providing a prepolymer, wherein the relative proportion of monomers in the mixture are selected to provide a prepolymer with a silicon content of from about 10% to about 30% by weight, of the prepolymer and a polar silicone-containing residue content of from about 30% to about 90% by weight of the prepolymer. In a further aspect, the at least one monomer having a siloxanyl group, and the at least one monomer having a polymerizable group can be the same monomer.

In a further aspect, the disclosed prepolymers can be prepared by a method comprising the steps of providing a mixture comprising at least one monomer having a siloxanyl group, wherein at least one of the at least one monomer having a siloxanyl group is a polar silicone-containing monomer further comprising at least one polar moiety; at least one monomer having a polymerizable group (e.g., vinyl methacrylate, which has two polymerizable groups having different polymerizabilities); optionally, at least one comonomer (e.g., HEMA); and, optionally, at least one monomer having a hydrophilic group; reacting the monomers by heating the mixture at a reaction temperature (e.g., from about 50° C. to about 60° C.) for a reaction time (e.g., from about 2 hours to about 6 hours), and/or exposing the mixture to a radical initiator (e.g., 2,2'-azobis(2,4-dimethylvaleronitrile)), thereby providing a prepolymer, wherein the relative proportion of monomers in the mixture are selected to provide a prepolymer with a silicon content of from about 10% to about 30% by weight, of the prepolymer and a polar silicone-containing residue content of from about 30% to about 90% by weight of the prepolymer.

It is understood that solvent can be removed (e.g., by evaporation) after production of the intermediate polymer and/or after production of the prepolymer. It is also understood that either or both of the intermediate polymer and the prepolymer can be purified by, for example, washing, filtration, and/or distillation. Purification can be accomplished by, for example, conventional distillation or by reduced pressure distillation (e.g., thin film distillation), optionally in the presence of a polymerization inhibitor, for example, one or more of an alkylhydroquinone or a hydroxynaphthalene. That is, in a further aspect, the disclosed prepolymers can be purified by removing lower molecular weight impurities by distillation, for example, reduced pressure distillation. Such a purification method can comprise the steps of: (1) providing a prepolymer mixture or a crude prepolymer, and (2) reduced pressure distillation of lower molecular weight impurities from the prepolymer mixture or the crude prepolymer in the presence of at least one polymerization inhibitor comprising an alkylhydroquinone or a hydroxynaphthalene. In a further aspect, the method further comprises the step of collecting the distilled siloxanyl monomer. The monomer can be collected, for example, in a receiving vessel. In one aspect, the polymerization inhibitor can comprise one or more of an alkylhydroquinone or a hydroxynaphthalene.

Typically, after the intermediate polymer or prepolymer has been formed, substantially all unreacted reactants and byproducts are removed. By "substantially all," it is meant that less than about 0.1 weight % remains after purification. This can be done by conventional means, such as ultrafiltration. However, it is possible to purify the intermediate polymer or prepolymer by swelling with water and rinsing with water to remove substantially all of the undesired constituents including monomeric, oligomeric, or polymeric starting compounds and catalysts used in the preparation and byproducts formed during the preparation of the intermediate polymer or prepolymer. The washing can be conducted with deionized water and conditions can be selected to provide a large surface to volume ratio of the intermediate polymer or prepolymer particles. This can be done by freeze drying the intermediate polymer or prepolymer, making a thin film from the intermediate polymer or prepolymer, extruding the intermediate polymer or prepolymer into rods, nebulizing the intermediate polymer or prepolymer solution into the deionized water, and other like methods, which are known to those skilled in the art.

In a further aspect, a polymerizable residue can be obtained by reacting a unit having a structure represented by the formula:

wherein $R^z$ represents hydrogen or methyl; wherein Z represents an optionally substituted $C_1$-$C_{20}$ alkyl residue or an optionally substituted $C_6$-$C_{20}$ aryl residue, which alkyl or aryl further comprises at least one of an hydroxyl group, a carboxyl group, an ester group, or a carboxylic anhydride group; with at least one compound having at least one polymerizable residue.

D. Compositions

In one aspect, the prepolymers can be used to prepare further polymers by, for example, a thermally-initiated or photo-initiated polymerization or crosslinking reaction. Accordingly, in a further aspect, the invention relates to a polymer obtained by polymerizing or cross-linking one or more of the disclosed prepolymers.

Additionally, the disclosed polymers can be used to prepare medical devices, such as ophthalmic lenses, for example contact lenses, intraocular implants, and artificial cornea; stents, implants, and catheters; and other optical devices. Accordingly, in a further aspect, the invention relates to an ophthalmic lens, contact lens, intraocular implant, artificial cornea, stent, implant, catheter; or other optical device obtained by polymerizing or cross-linking one or more of the disclosed prepolymers.

E. Applications of the Compositions

The present invention provides a material from which molded plastics having a satisfactory oxygen permeability, satisfactory hydrophilicity and satisfactory resistance to breakage may be produced by polymerizing the material. The molded plastics are useful as drug adsorbents used for drug delivery, and ophthalmic lenses such as contact lenses, intraocular lenses, artificial cornea and spectacle lenses. Among these, they are particularly suited for contact lenses.

In one aspect, the compositions can provide materials for producing molded plastics, which material is excellent in compatibility with hydrophilic monomers such as 2-hydroxyethyl methacrylate, which is capable of yielding molded plastics, by polymerizing the material, having satisfactory oxygen permeability, satisfactory hydrophilicity, and a low modulus of elasticity, as well as excellent optical quality.

By the present invention, a material for producing molded plastics may be provided, which material is excellent in compatibility with hydrophilic monomers such as, but not limited to 2-hydroxyethyl methacrylate, N-vinyl pyrrolidone, N,N-dimethylacrylamide, N-vinyl-N-methyl acetamide combinations thereof and the like which is capable of yielding molded plastics, by polymerizing the material, having a satisfactory oxygen permeability, satisfactory hydrophilicity and a low modulus of elasticity, as well as excellent optical quality.

In one aspect, the compounds and compositions of the invention can be used to provide a molded article comprising at least one of the compositions of the invention. In a further aspect, the compounds and compositions of the invention can be used to provide an ophthalmic lens comprising at least one of the compositions of the invention. In a yet further aspect, the compounds and compositions of the invention can be used to provide a contact lens comprising at least one of the compositions of the invention.

Molded articles, e.g. contact lenses, can be prepared by further polymerizing or crosslinking the disclosed prepolymers, either alone or with one or more other of the comonomers or materials described herein. For preparing the molded articles, especially ophthalmic lenses, additional materials may also be included in the polymerization mixture. For example, a crosslinker having two or more polymerizable carbon-carbon unsaturated bonds in the molecule can be included to obtain good mechanical properties and good resistance to antiseptic solutions and washing solutions. The percentage of the crosslinker, based on the total monomers to be copolymerized, is preferably not less than about 0.01% by weight, more between about 0.05% and about 15% by weight, still more preferably between about 0.1% and about 5% by weight. In certain aspects, because the disclosed prepolymers comprise polymerizable moieties, additional crosslinker may be omitted.

From the viewpoint of simultaneously attaining a satisfactory oxygen permeability and satisfactory hydrophilicity, the percentage of the material for producing molded plastics according to the present invention in the prepared molded plastics is, in cases where other siloxanyl-group containing polymerizable material is not copolymerized, preferably from about 30% by weight to about 100% by weight, more preferably from about 50% by weight to about 99% by weight, still more preferably from about 60% by weight to about 95% by weight. In cases where one or more other siloxanyl group-containing polymerizable materials are copolymerized, the percentage of the total of the material according to the present invention and the other siloxanyl group-containing polymerizable material(s) in the prepared molded plastics is preferably from about 30% by weight to about 100% by weight, more preferably from about 50% by weight to about 99% by weight, still more preferably from about 60% by weight to about 95% by weight.

The molded plastics may contain additional components, including, but not limited to UV absorbers, colorants, coloring agents, wetting agents, slip agents, pharmaceutical and nutraceutical components, compatibilizing components, antimicrobial compounds, release agents, combinations thereof and the like. Any of the foregoing may be incorporated in non-reactive, polymerizable, and/or copolymerized form.

In the polymerization or crosslinking for preparing molded articles, it is preferred to add a thermal polymerization initiator or photopolymerization initiator typified by peroxides and azo compounds for easily attaining polymerization. In cases where thermal polymerization is carried out, one having the optimum decomposition characteristics at the satisfactory reaction temperature is selected. In general, azo initiators and peroxide initiators having a 10 hour half-life temperature of from about 40° C. to about 120° C. are preferred. Examples of the photoinitiator include carbonyl compounds, peroxides, azo compounds, sulfur compounds, halogenated compounds and metal salts. These polymerization initiators can be used individually or in combination. The amount of the polymerization initiator(s) can be up to about 1% by weight based on the polymerization mixture.

In (co)polymerizing the material for producing molded plastics according to the present invention, a polymerization solvent can be used. As the solvent, various organic and inorganic solvents can be employed. Examples of the solvents include water; alcoholic solvents such as methyl alcohol, ethyl alcohol, normal propyl alcohol, isopropyl alcohol, normal butyl alcohol, isobutyl alcohol, tert-butyl alcohol, ethylene glycol, diethylene glycol, triethylene glycol, tetraethylene glycol and polyethylene glycol; glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether and polyethylene glycol dimethyl ether; ester solvents such as ethyl acetate, butyl acetate, amyl acetate, ethyl lactate and methyl benzoate; aliphatic hydrocarbon solvents such as normal hexane, normal heptane and normal octane; alicyclic hydrocarbon solvents such as cyclohexane and ethylcyclohexane; ketone solvents such as acetone, methyl ethyl ketone and methyl isobutyl ketone; aromatic hydrocarbon solvents such as benzene, toluene and xylene; and petroleum solvents. These solvents can be used individually or two or more of these solvents can be used in combination.

As the method of polymerization of the material for producing molded articles according to the present invention, and as the method of molding the plastics, known methods can be employed. For example, a method in which the material is once polymerized and molded into the shape of round bar or plate and the resulting round bar or plate is then processed into the satisfactory shape by cutting or the like, mold polymerization method and spin cast polymerization method can be employed.

As an example, a process for producing an ophthalmic lens from the disclosed prepolymers will now be described. First, a gap having a prescribed shape, between two mold parts, is filled with a prepolymer composition and photopolymerization or thermal polymerization is carried out to shape the composition into the shape of the gap between the molds. The molds are made of a resin, glass, ceramics, metal, or the like. In case of photopolymerization, an optically transparent material is used, and a resin or glass is usually used. In case of producing an ophthalmic lens, a gap is formed between two mold parts facing each other, and the gap is filled with the material composition. Depending on the shape of the gap and on the properties of the material composition, a gasket may be used in order to give the ophthalmic lens a prescribed thickness and to prevent leakage of the material composition filled in the gap. The molds containing the gap filled with the material composition are then irradiated with an actinic radiation such as ultraviolet light, visible light or a combination thereof, or placed in an oven or bath to heat the material composition, thereby carrying out polymerization. The two polymerization methods may be employed in combination, that is, thermal polymerization may be carried out after photopolymerization, or photopolymerization may be carried out after thermal polymerization. In photopolymerization embodiment, a light containing ultraviolet light, such as the light from a mercury lamp or UV lamp (e.g., FL15BL, TOSHIBA corporation) is radiated for a short time (usually not longer than 1 hour). In cases where thermal polymerization is carried out, it is preferred to employ conditions in which the composition is slowly heated from room temperature to a temperature from about 60° C. to about 200° C. over a period of several hours to several tens hours, in view of the optical uniformity, high quality, and high reproducibility of the ophthalmic lens.

The molded articles produced from the disclosed prepolymer can have a dynamic contact angle (during forward movement, immersion rate: about 0.1 mm/sec) of, for example, not more than about 130°, more preferably not more than about 120°, still more preferably not more than about 100°. The water content thereof is preferably from about 3% to about 50%, more preferably from about 5% to about 50%, still more preferably from about 7% to about 50%. From the viewpoint of the wearer when the ophthalmic lens is used as a contact lens, the higher the oxygen permeability, the better. The oxygen permeability coefficient $[\times 10^{-11}(cm^2/sec)mLO_2/(mL \cdot hPa)]$ is preferably not less than about 50, more preferably not less than about 60, still more preferably not less than about 65. In certain aspects, the oxygen permeability coefficient can be at least about 90, at least about 95, at least about 100, at least about 105, or at least about 110. The tensile modulus of elasticity is preferably from about 0.01 to about 30 MPa, more preferably from about 0.1 to about 7 MPa. The tensile elongation is preferably not less than about 50%, more preferably not less than about 100%. Since a higher tensile elongation gives higher resistance to breakage, it is preferred that the molded plastics have a high tensile elongation. These properties may be measured using the test methods disclosed in WO03/022321.

The molded articles can also be useful as drug carriers used for drug delivery, and ophthalmic lenses such as contact lenses, intraocular lenses, artificial cornea, and spectacle lenses. Among these, they are particularly suited for ophthalmic lenses such as contact lenses, intraocular lenses, and artificial cornea. Among these, they are particularly suited for ophthalmic lenses, especially contact lenses.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. ANALYTICAL METHODS

Molecular weight: size exclusion chromatography (SEC) equipment is composed of a column oven at 40° C., a PE LC-410 pump with PE Nelson 900A/D and a series 200 autosampler. The detector can be a RI Merck L7490. The column combination can consist of two TSK-Gel columns from TosoHaas (G4000PW+G2500PW) and a guardcolumn. The eluent can be made with methanol-water (75/25 wt/wt) and adjusted to 50 mM sodium chloride (NaCl). The flow rate can be 0.5 mL/minute. The injection volume is 150 μL and the run time can be 60 minutes. A calibration curve can be obtained with third order regression using PEG and PEO of Peak molecular weights ranging from 960000 to 194 as standard references. These polymer standards can be purchased from Polymer Laboratories Inc, Amherst Mass. (Calibration kits PEG-10 part No 2070-0100; PEO-10 part No 2080-0101). Added standard reference PEG of Peak molecular weight of 194 gives a flow signal at a well-defined position, which can be used as an internal standard or fixation point. Added NaCl can play the same role and gives a second fixation point. Peak integrations can be made manually. Integration start and end points can be manually determined from significant difference on global baseline. The injection solutions can be prepared with methanol-water 75/25 wt/wt adjusted to 60 mM NaCl to give a polymer concentration of 2 mg/mL. Tetraethylene glycol can be added to the sample in a concentration of 1 mg/ml in order to give a peak flow reference. The solutions are filtered on 0.5 μm disposable filters before the injection is performed. Polydispersity, $P_d$, of a polymer sample can be defined as $P_d=M_w/M_n$. The peak molecular weight, $M_p$, is the molecular weight of the highest peak in the molecular weight distribution curve.

Figure 1:
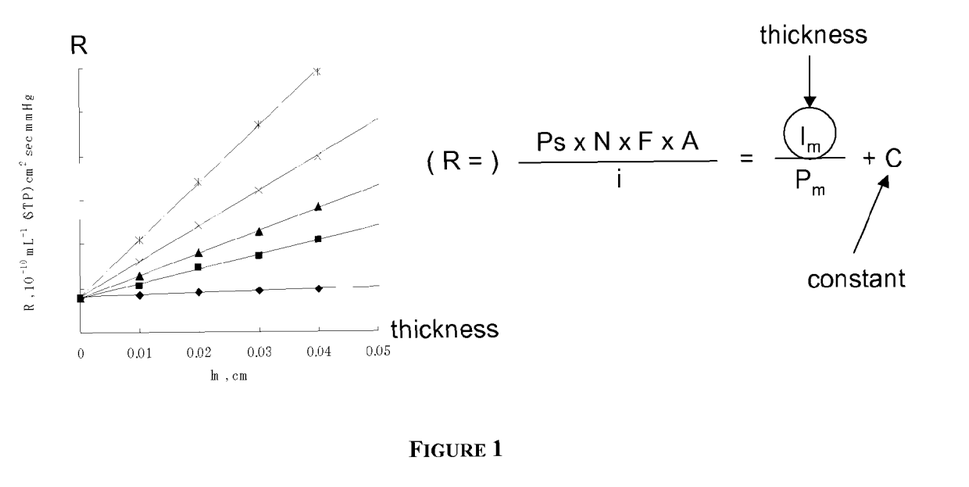
FIG. 1 shows a plot of R (1/Q) versus thickness (lm).
Figure 2:
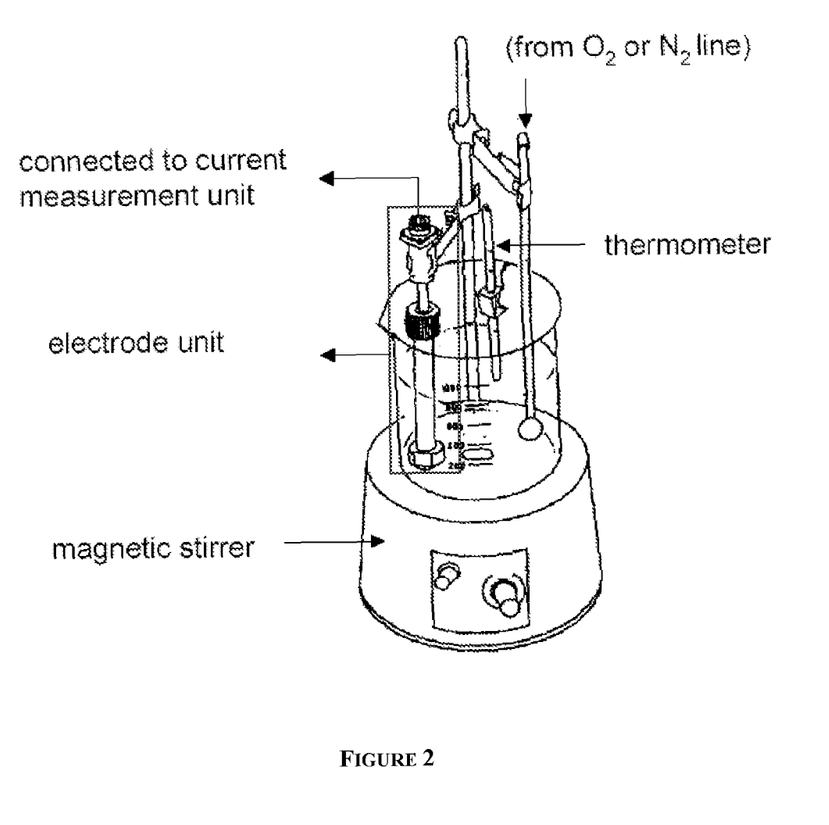
FIG. 2 shows an apparatus for oxygen permeability measurement.
Figure 3:
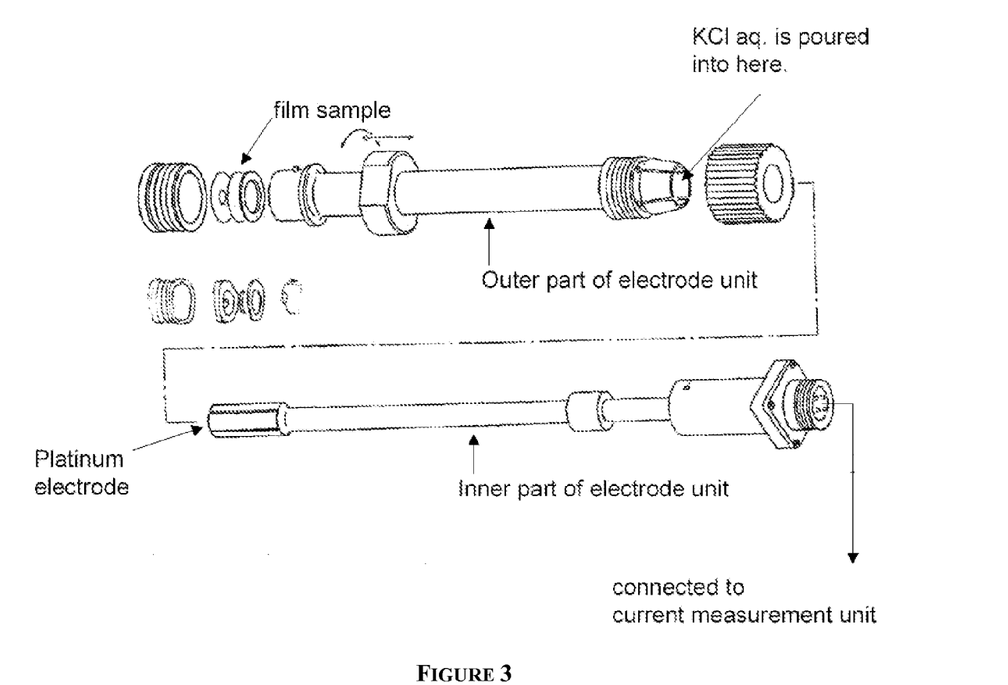
FIG. 3 shows the structure of an electrode unit used to measure oxygen permeability.
Figure 4:
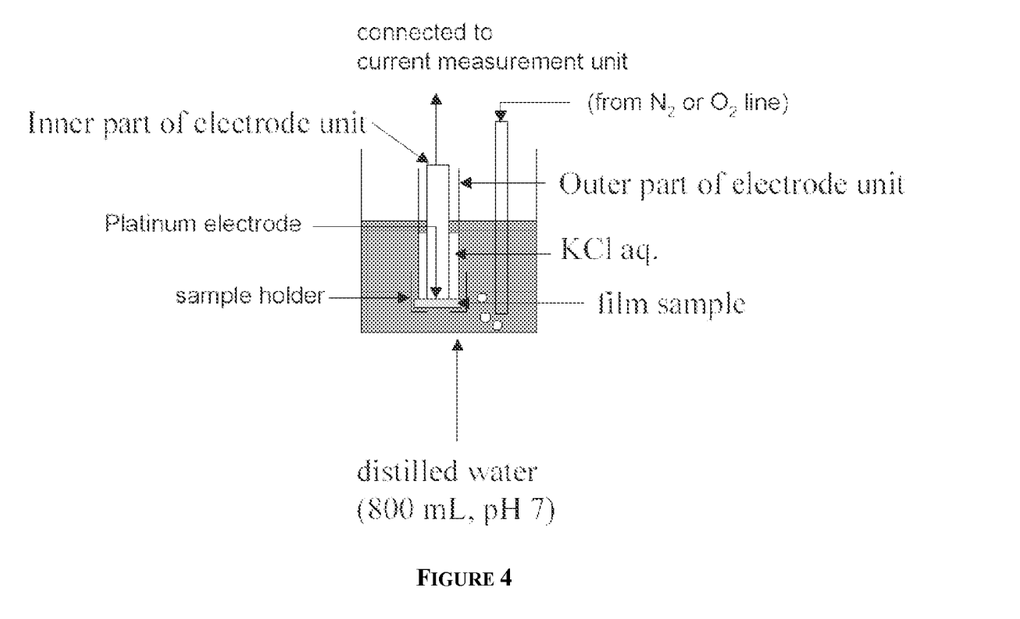
FIG. 4 shows a schematic of an oxygen permeability measurement setup.

Oxygen permeability: A sample's oxygen permeability coefficient was determined by using a Seikaken-shiki film oxygen permeability meter manufactured by RIKA SEIKI KOGYO CO., LTD. The oxygen permeability coefficient of a sample in the form of a film was measured in water at 35° C. (temperature controller not shown in Figure). Stirring was performed at a rate of 800 rpm with a 3 mm octagon-type MAGMIX magnetic stirrer (Mitamura Riken Kogyo Inc.). Four film samples with different thickness were prepared (0.1 mm, 0.2 mm, 0.3 mm, and 0.4 mm; diameter 16 mm). The four samples with different thickness were measured to determine Pm of every example (see FIG. 1); the graduation of the dial upright gauge used was 0.001 mm; with an accuracy of about ±0.003 mm. One of the samples was set on an electrode. 0.5 N KCl (aqueous) was poured into the electrode as an electrolytic solution (see FIGS. 2-4). The electrode was set in distilled water (pH=7, volume=800 ml). At first, the current under nitrogen bubbling (flow rate=100 mL/min.; electric current, i, is measured after it is in equilibrium) was measured in order to adjust zero. Then the current under oxygen bubbling was measured. R was calculated by the following formula: $R=(Ps \times N \times F \times A)/i$ [$cm^2$ sec mmHg/mL (STP)] (wherein Ps=760 mmHg (atmospheric pressure), N=4 (the number of electrons which involves a reaction at the electrode), F=96500 coulomb/mol (Faraday constant), A=area of the electrode ($cm^2$), i=measured current (uA)). R involves constant (not proportional) part, so plural measurement and plotting are necessary to determine Pm (see FIG. 1). R versus the thickness of the samples was plotted. The inverse of the slope is the oxygen permeability coefficient (Pm).

In oxygen permeability testing, edge correction is typically considered when the area of a material through which oxygen passes differs from one surface of the sample to the other surface. In the present measurement method, the area of the hole of the ring which is set next to a film sample (see FIG. 3, upper left portion) is the same as the area of platinum electrode, so edge correction is unnecessary.

Moisture Content: a sample in the form of a film sizing about 10 mm×10 mm×0.2 mm was used. The sample was dried in a vacuum dryer at 40° C. for 16 hours, and the weight (Wd) of the sample was measured. Thereafter, the resulting sample was immersed in pure water at 40° C. in a thermostat bath overnight or more, and the moisture on the surface was wiped with Kimwipe, followed by measurement of the weight (Ww). The moisture content was calculated according to the following equation:

$$\text{Moisture Content (\%)} = 100 \times (Ww-Wd)/Ww$$

Tensile Test: a sample in the form of a film sizing about 19.5 mm×15 mm×0.2 mm was used. The tensile modulus of elasticity was measured using Tensilon type RTM-100 manufactured by ORIENTEC. The speed of pulling was 100 mm/min and the distance between grips was 5 mm.

2. EXAMPLE 1

To a 300 mL three-necked flask equipped with a thermometer, three way stopcock, and mechanical stirrer, 51.14 g of a silicone monomer (SiMAA) represented by the following Formula (h):

15.2 g of a silicone monomer (mPDMS, average molecular weight: about 1000):

18.42 g of N,N-dimethylacrylamide (DMA), 6.12 g of 2-hydroxyethyl methacrylate (HEMA), 2,2'-azobis(2,4-dimethylvaleronitrile) (ADVN), 2.04 g of 2-(2'-hydroxy-5'-methacryloxyethylphenyl)-2H-benzotriazole (UV absorber), 0.0204 g of a dye represented by the following Formula (r):

0.93 g of 1-dodecylmercaptan (DSH), and t-amyl alcohol (TAA) were added, and the atmosphere was replaced with argon. The mixture was stirred under argon atmosphere at 50° C. for 0.5 hours and then at 60° C. for 4.5 hours, thereby polymerizing the monomers. After completion of the reaction, the solvent was evaporated with an evaporator. The obtained solids were dissolved in 150 mL of methanol under heat, and the resulting solution was added to 300 mL of 40% (v/v) aqueous methanol solution under stirring. The resulting mixture was left to stand and the supernatant was removed. The obtained precipitate was washed once with 300 mL of 65% (v/v) aqueous methanol solution and once with 300 mL of 75% (v/v) aqueous methanol solution. The obtained solids were dried under vacuum at 40° C. for 18 hours, and then pulverized after adding liquid nitrogen, followed by drying at 40° C. for 3 hours to obtain an unfunctionalized polymer.

To a 300 mL four-necked flask, 65 g of the obtained unfunctionalized polymer, 69 mg of 2,6-di-t-butyl-4-methylphenol (BHT) and 220 g of 1,4-dioxane were added, and a mechanical stirrer, a connecting tubule connected to a nitrogen line, and a Claisen tube were mounted, and a Liebig condenser, siphon and eggplant type flask were connected to the tip of the Claisen tube. The temperature was raised to 110° C. while stirring the mixture under nitrogen gas flow, and the temperature of 110° C. was kept until about 110 g of 1,4-dioxane was evaporated, thereby eliminating moisture from the reaction system. After cooling the mixture to 60° C., 30 μL of dibutyltindilauric acid (DBTDL) and 3.40 g of 2-isocyanate ethyl methacrylate (MOI) were added under nitrogen gas flow, and the resulting mixture was allowed to react at 60° C. for 3 hours. After completion of the reaction, 50 mL of methanol was added, and the mixture was stirred for 15 minutes. The reaction solution was concentrated in an evaporator at 50° C., and 100 mL of methanol was added to the obtained concentrate to form a uniform solution. The resulting solution was added to 300 mL of 70% (v/v) aqueous methanol solution under stirring, and the mixture was left to stand, followed by removal of the supernatant. The precipitate was further washed twice with 300 mL of 85% (v/v) aqueous methanol solution. The obtained solids were dried under vacuum at 40° C. for 18 hours, and then pulverized after adding liquid nitrogen, followed by drying at 40° C. for 3 hours to obtain the desired silicone polymer.

3. EXAMPLES 2-5

The same operations as in Example 1 were repeated except that the composition of the polymerization mixture was changed as shown in Table 1. The UV absorber, dye (r), DBTDL and BHT, which are not shown in Table 1, were used in the same ratio as in Example 1.

In Table 1, Formula (j) is as follows, which shows a polar silicone monomer:

and Formula (k) is as follows, which shows a polar silicone monomer:

4. COMPARATIVE EXAMPLES 1 TO 5

The same operations as in Example 1 were repeated except that the composition of the polymerization mixture was changed as shown in Table 1. In Comparative Examples 1, 3 and 4, the UV absorber, dye (p), DBTDL and BHT were used in the same ratio as in Example 1. In Comparative Examples 2 and 5, only the solubilities were confirmed, and functionalization was not performed.

5. EXAMPLE 5

To 4.49 g of a solution containing 0.49 g of polyvinylpyrrolidone K90 dissolved in polyethylene glycol 200, 5.51 g of the silicone prepolymer or the unfunctionalized polymer obtained in any one of Examples 1 to 4 and Comparative Examples 1 and 2 was added, and the materials were mixed under heat at 70° C., followed by reducing the pressure to carry out degassing. The solubility was visually observed, and the results are shown in Table 1.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

TABLE 1

|  | Example 1 | Example 2 | Example 3 | Example 4 | Comparative Example 1 | Comparative Example 2 | Comparative Example 3 | Comparative Example 4 | Comparative Example 5 |
| --- | --- | --- | --- | --- | --- | --- | --- | --- | --- |
| Polar Silicone Monomer | Formula (h) | Formula (h) |  | Formula (k) | Formula (h) | Formula (h) |  | Formula (h) |  |
| (g) | 51.14 | 33.44 |  | 19 | 25 | 32 |  | 16.72 |  |
| Polar Silicone Monomer |  | Formula (j) | Formula (j) |  |  |  |  | Formula (j) |  |
| (g) |  | 36.00 | 60.97 |  |  |  |  | 18.00 |  |
| Non-polar Silicone Monomer | Formula (i) |  |  | Formula (i) | Formula (i) |  | TRIS |  | Formula (i) |
| (g) | 15.28 |  |  | 3.51 | 31.47 |  | 56 |  | 62 |
| Hydrophylic Monomer | DMA | DMA | DMA | DMA | DMA |  | DMA | DMA |  |
| (g) | 18.42 | 15.48 | 23.87 | 9.00 | 28.37 |  | 28.84 | 53.63 |  |
| Linker Monomer | HEMA | HEMA | HEMA | HEMA | HEMA |  | HEMA | HEMA |  |
| (g) | 6.12 | 6.12 | 6.12 | 2.27 | 6.12 |  | 6.12 | 6.12 |  |
| Polymerization Initiator | ADVN | ADVN | ADVN | ADVN | ADVN | ADVN | ADVN | ADVN | ADVN |
| (g) | 0.093 | 0.0093 | 0.0093 | 0.0046 | 0.0093 | 0.032 | 0.0093 | 0.0093 | 0.093 |
| Chain Transfer Agent | DSH | DSH | DSH | DSH | DSH | DSH | DSH | DSH | DSH |
| (g) | 0.837 | 0.651 | 0.744 | 0.2764 | 0.651 | 0.32 | 0.837 | 0.651 | 0.651 |

TABLE 1-continued

|  | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| Polymerization Solvent | TAA | TAA | TAA | TAA | TAA | TAA | TAA | TAA | TAA |
| (g) | 93 | 93 | 93 | 34.55 | 93 | 48 | 93 | 93 | 93 |
| Compound Having Polymerizable Group | MOI | MOI | MOI | MOI | MOI |  | MOI | MOI |  |
| (g) | 3.40 | 1.70 | 2.55 | 1.16 | 3.40 |  | 3.40 | 3.40 |  |
| Silicon Content(%) | 15.9 | 16.1 | 14.9 | 14.0 | 15.8 | 19.9 | 18.7 | 7.6 | 31.5 |
| Total Amount of Polar Silicone Monomers(%) | 54 | 75 | 65 | 54 | 26 | 100 | 0 | 35 | 0 |
| Oxygen Permeability | 108 | 113 | 97 | 90 | 105 | — | 139 | 49 | — |
| Solubility in PVP/PEG Solution | Soluble | Soluble | Soluble | Soluble | Insoluble | Insoluble | Insoluble | Soluble | Insoluble |

What is claimed is:

1. A silicone prepolymer comprising:
at least one silicone-containing residue having a structure represented by the formula:

wherein $R^a$ represents hydrogen or methyl, and
wherein A represents a siloxanyl group, wherein at least one A has a structure represented by the formula:

wherein L represents a $C_1$-$C_{20}$ alkyl residue or a $C_6$-$C_{20}$ aryl residue; and
wherein D represents a siloxanyl group having a structure represented by the formula:

wherein $E^1$ to $E^{11}$ independently represent hydrogen, $C_1$-$C_{20}$ alkyl residue, or $C_6$-$C_{20}$ aryl residue;
wherein h represents an integer of from 0 to 200; and
wherein i, j, and k independently represent integers of from 0 to 20, with the proviso that h, i, j and k are not simultaneously zero; and at least one polymerizable residue having a structure represented by the formula:

wherein $R^p$ represents hydrogen or methyl, and
wherein P represents an organic group comprising at least one polymerizable moiety selected from a methacryloyloxy group, an acryloyloxy group, a methacryl amide group, an acryl amide group, a styryl group, a vinyl group, a vinyl carbonate group, a vinyl carbamate group, an allyl carbonate group, or an allyl carbamate group;
wherein the prepolymer has a silicon content of from about 10% to about 30% by weight, of the prepolymer; and
wherein the total of the polar silicone units is from about 50% to about 80% by weight, based on solid content of the prepolymer.

2. The prepolymer of claim 1, further comprising at least one hydrophilic residue having a structure represented by the formula:

wherein $R^b$ represents hydrogen or methyl; and
wherein B represents a hydrophilic group.

3. The prepolymer of claim 2, wherein the hydrophilic residue comprises one or more residues of N,N-dimethylacrylamide, 2-hydroxyethyl methacrylate, N-vinylpyrrolidone, N-vinylformamide, N-vinylacetamide, (meth)acrylic acid, N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, or N-vinylimidazole.

4. The prepolymer of claim 1, wherein at least one A has a structure represented by the formula:

wherein n represents an integer of from 3 to 10; and
wherein $R_s$ represents a $C_1$-$C_{20}$ alkyl residue or a $C_6$-$C_{20}$ aryl residue.

5. The prepolymer of claim 1, wherein the polymerizable residue is obtained by reacting a unit having a structure represented by the formula:

wherein $R^z$ represents hydrogen or methyl;

wherein Z represents an optionally substituted $C_1$-$C_{20}$ alkyl residue or an optionally substituted $C_6$-$C_{20}$ aryl residue, which alkyl or aryl further comprises at least one of an hydroxyl group, a carboxyl group, an ester group, or a carboxylic anhydride group;

with at least one compound having at least one polymerizable residue.

6. The prepolymer of claim 5, wherein Z comprises one or more of:

a halogenocarbonyl group, a (meth)acryloyloxycarbonyl group, a carboxyl group, a $C_1$-$C_{20}$ alkyloxycarbonyl group, a 2-aminoethoxycarbonyl group, a 4-halogenocarbophenyl group, a 4-carboxyphenyl group, or a 4-($C_1$-$C_{20}$ alkyloxycarbonyl)phenyl group.

7. The prepolymer of claim 5, wherein the compound having at least one polymerizable group is 2-isocyanatoethyl (meth)acrylate, (meth)acryloyl isocyanate, (meth)acrylic acid halide, (meth)acrylic anhydride, (meth)acrylic acid, methyl(meth)acrylate, ethyl(meth)acrylate, 2-hydroxyethyl(meth)acrylate, 2-aminoethyl(meth)acrylate, 4-vinylbenzoic acid halide, 4-vinylbenzoic anhydride, or 4-vinylbenzoic acid ester.

8. The prepolymer of claim 1, wherein at least one polymerizable moiety has a structure represented by the formula:

wherein R represents hydrogen or methyl.

9. The prepolymer of claim 1, wherein the prepolymer has a silicon content of from about 13% to about 20% by weight.

10. The prepolymer of claim 1, wherein the content of the polymerizable unit is from about 0.1 to about 15 mol %, based on the prepolymer.

11. The prepolymer of claim 1, wherein the prepolymer has a solubility of not less than about 50% by weight, based on solid content of the prepolymer, in a water-soluble solvent.

12. The prepolymer of claim 11, wherein the water-soluble solvent comprises one or more of ethylene glycol, propylene glycol, polyethylene glycol, polypropylene glycol, or ethylene glycol-propylene glycol copolymer or a mixture thereof.

13. The prepolymer of claim 1, wherein the prepolymer has a solubility of not less than about 50% by weight, based on solid content of the prepolymer, in a water-soluble solvent comprising from about 1% to about 10% by weight of polyvinylpyrrolidone.

14. A polymer obtained by polymerizing the prepolymer of claim 1.

15. An ophthalmic lens comprising the polymer according to claim 14.

16. A contact lens comprising the polymer according to claim 14.

* * * * *